United States Patent [19]

Johnson-Flanagan et al.

[11] Patent Number: 5,773,692

[45] Date of Patent: Jun. 30, 1998

[54] ANTI-SENSE RNA FOR CAB TRANSCRIPT TO REDUCE CHLOROPHYLL CONTENT IN PLANTS

[75] Inventors: Anne M. Johnson-Flanagan, Edmonton; Jas Singh, Nepean; Laurian S. Robert, Gatineau; Janice Carole Politeski Morissette, Wainwright, all of Canada

[73] Assignee: Her Majesty the Queen in right of Canada, as represented by Agriculture and Agri-Food Canada, Ontario, Canada

[21] Appl. No.: 570,929

[22] Filed: Dec. 12, 1995

[51] Int. Cl.$^6$ .......................... C12N 15/29; C12N 15/82; A01H 4/00; A01H 5/00

[52] U.S. Cl. ...................... 800/205; 536/23.1; 536/24.5; 435/91.1; 435/91.3; 435/320.1

[58] Field of Search .................................. 536/23.1, 24.1, 536/24.5; 435/91.31, 91.1, 320.1; 800/205

[56] References Cited

PUBLICATIONS

Boivin et al. Genome vol. 36, pp. 139–146, 1993. Isolation of Lhcb3 seuences from Brassica napus: evidence for conserved genes encoding LHCII type III chloropyll a/b binding proteins.

Pichersky et al. Plant Molecular Biology 9: 205–216, 1987. Molecular characterization and genetic mapping of DNA sequences encoding the Type I chlorophyll a/b binding polypeptide of photosystem I in Lycopersicon esculentum (tomato).

Cashmore, Anthony R., *Structure and expression of a pea nuclear gene encoding a chlorophyll a/b binding polypeptide*. Proc. Natl. Acad. Sci., USA. vol. 81, pp. 2960–2964, May (1984) Biochemistry.

Flachmann, Ralf et al., *Accumulation of Plant Antenna Complexes is Regulated by Post–Transcriptional Mechanisms in Tobacco*. The Plant Cell, vol. 7, pp. 149–160, Feb. (1995).

Politeski, J.C. et al., *Reducing Chlorophyll Accumulation in Transgenic Brassic Napus Seeds*. Supplement to Plant Physiology, vol. 105, No. 1, May (1994).

Johnson–Flanagan, A.M. et al., *Degreening in Canola (Brassica napus, cv. Westar) Embryos under Optimum Conditions*. J. Plant Physiol. vol. 136, pp. 180–186, (1990).

Johnson–Flanagan, A.M. et al., *The Impact of Sublethal Freezing during Maturation on Pigment Content in Seeds of Brassica napus*. J. Plant Physiol. vol. 136, pp. 385–390, (1990).

Johnson–Flanagan, A.M. et al., *A Method to Study Seed Degreening Using Haploid Embryos of Brassica napus cv. Topas*. J. Plant Physiol. vol. 141, pp. 487–493, (1993).

Johnson–Flanagan, A.M. et al., *Peroxidase–mediated chlorophyll bleaching in degreening canola (Brassica napus) seeds and its inhibition by sublethal freezing*. Physiologia Plantarum 80, pp. 453–459, Copenhagen (1990).

Johnson–Flanagan, A.M. et al., *The impact of freezing during maturation on storage products in canola seeds*. Physiologia Plantarum, 81:301–308 (1991).

*Primary Examiner*—Douglas W. Robinson
*Assistant Examiner*—Thomas Haas
*Attorney, Agent, or Firm*—Oliff & Berridge, PLC

[57] ABSTRACT

The initial steps in photosynthesis are the conversion of light energy into chemical energy. This conversion is performed by the multisubunit protein-pigment complexes of the thylakoid membranes. Oxygen-evolving photosystems contain photosystem I (PSI) and photosystem II (PSII), which act in tandem. In PSII, the majority of light-adsorbing chlorophylls are attached to LHCII, the light harvesting complex associated with this photosystem. LHCII is the most abundant member of the family of chlorophyll a/b binding (CAB) proteins. A gene encoding a type I chlorophyll a/b binding protein of LHCII (ICABPSII) has been cloned from *Brassica napus* L. An anti-sense RNA of this gene has been used to reduce the amount of chlorophyll a/b binding protein and thus reduce the amount of chlorophyll in the resulting transgenic plants. By using "site" specific promoters the reduction of chlorophyll can be targeted to specific organelles in the transgenic plant and thus can be used to reduce the green color at these sites. Thus it is possible to use the anti-sense RNA of a chlorophyll a/b binding protein as a means for degreening, for example fruits, seeds or floral parts in transgenic plants.

15 Claims, 2 Drawing Sheets

```
GAATTCCACT TCA ATG GCC TCT TCA ACA ATG GCT CTC TCC TCC CCT GCC   49
TTC GCT GGA AAG GCC GTG AAG CTT TCT CCT GCA GCA TCA GAA GTC CTT   97
GGA AGC GGC CGT GTG ACA ATG AGG AAG ACC GTC GCC AAG CCA AAG GGA  145
CAA TCA GGC AGC CCA TGG TAC GGT TTC GAA AGA GTC AAG TAC TTG GGT  193
CCA TTC TCT GGC GAG CCA CCG AGC TAC CTT ACC GGA GAG TTC CCA GGA  241
GAC TAC GGA TGG GAC ACC GCA GGC CTC TCA GCC GAT CCC GAG ACA TTC  289
GCA AGG AAC CGT GAG CTA GAA GTT ATC CAC TGC AGG TGG GCC ATG CTT  337
GGA GCC CTA GGC TGT GTC TTC CCG GAG TTG TTG CTA GG AAC GGA GTC  385
AAG TTC GGA GAG GCG GTT TGG TTC AAG GCC GGC TCA CAG ATC TTC AGC  433
GAA GGA GGA CTT GAC TAC TTG GGC AAC CCG GGC TTA GTC CAC GCT CAG  481
AGC ATC TTA GCC ATT TGG GCC ACT CAG GTG ATC CTC ATG GGA GCT GTT  529
GAG GGT TAC AGA GTC GCC GGA GAG GGA CCA TTG GGA GAA GCA GAG GAC  577
TTG CTA TAC CCA GGA GGC AGC TTC GAC CCA TTG GGC CTT GCT ACC GAC  625
CCA GAG GCT TTC GCC GAG TTG AAG GTG AAG GAG ATC AAG AAC GGG AGA  673
TTG GCT ATG TTC TCT ATG TTT GGA TTC TTT GTT CAA GCC ATT GTC ACT  721
GGT AAG GGA CCG TTG GAG AAC CTT GCT GAC CAT TTG GCT GAT CCA GTC  769
AAC AAC AAC GCT TGG GCC TTC GCC ACC AAC TTC GTT CCC GGA AAG TGA  817
GCGAAGTTTT ATTTTGTAAT TTGCTTCAGT CTTTTTGAAT TC                    859
```

The underlined sections are part of the linker DNA and do not form part of SEQ ID NO: 1

ANTI-SENSE RNA FOR CAB TRANSCRIPT TO REDUCE CHLOROPHYLL CONTENT IN PLANTS

FIELD OF INVENTION

The present invention relates to the application of recombinant DNA technology to plants, for the purpose of achieving transgenic plants with reduced chlorophyll content.

BACKGROUND OF THE INVENTION

The photosynthetic apparatus of plants is made up of two complexes, photosystem I and photosystem II, which are located in the thylakoid membranes of the chloroplast (Anderson, J. M., 1986, Annu. Rev. Plant Physiol. 37:93–136). Within these photosystems are the CAB proteins (chlorophyll a/b binding proteins), which are responsible for binding chlorophyll. There is a known correlation between the amount of chlorophylls and specific chlorophyll-binding proteins in leaves (Harpster et al., 1984, Plant Mol. Biol. 3:59–71). The level of control is transcriptional (Mayfield and Taylor (1984) Eur. J. Bioch. 144:79). Recently, it has been demonstrated that the same relationship exists between CAB proteins and chlorophyll in green haploid embryos and canola seed (Kennedy, J., M.Sc. Thesis , University of Alberta, Canada).

The CAB protein of PSII encoded by ICABPSII is the major light harvesting antenna associated with PSII and contains 40–60% of total chlorophyll in the mature chloroplast (Boardman et al. 1978, Current Topics in Bioenergetics, 8:35–109). Further, within PSII, there is a very high sequence homology between type I and type II CAB proteins (Pickersky et al., 1989, Plant Mol. Biol. 12:257). As such, targeting this gene will have a major effect on altering the chlorophyll content.

In certain circumstances it is desirable to reduce the level of chlorophyll in plants, specifically it is desirable to reduce the level of chlorophyll in specific organelles in plants. By way of example it may be desirable to reduce the amount of chlorophyll and thus the green colour in certain plant seeds, fruits, flower organs or other edible parts of the plants.

By way of specific example in rapeseed (Brassica napus, c.v. Westar, canola) during seed maturation the embryos undergo controlled degradative processes resulting in loss of chlorophyll. Both chlorophyll a and b degradation is biphasic. The breakdown products, chlorophyllide a and phenophytin a reach a peak during the period of rapid chlorophyll a degradation. Thereafter, loss of these pigments and chlorophyll a are linearly correlated. The relationship between chlorophyll b and its degradation products is not clear. However, this may reflect the low levels of these pigments in the seed rather than a lack of causal relationship. Furthermore, there is a gradual breakdown of the chlorophyll-protein complexes during degreening. The mature non-green seed does not contain any components of the photosystem.

Frequently, green seed in rapeseed is caused by sublethal freezing during seed maturation. A single frost in the range of 0° C. to −5° C. will lead to a green seed problem. Such a frost can occur at any stage of seed development, but the probability increases with the lateness of the season. Thus the green seed problem in the Canadian prairies is of special relevance, where an early fall frost is not uncommon.

Thus according to the present invention there is provided a method of reducing chlorophyll content in plants by reducing the amount of chlorophyll a/b binding protein in said plants.

SUMMARY OF THE INVENTION

According to the present invention there is provided a method of reducing chlorophyll content in plants by reducing the amount of chlorophyll a/b binding protein in said plants. Specifically the present invention relates to the use of anti-sense RNA and/or ribozyme RNA to reduce the chlorophyll content in plants by reducing the amount of chlorophyll a/b binding protein in said plants.

In one embodiment of the present invention there is provided a method of using anti-sense and/or ribozyme RNA to control the production of the CAB protein of PSII encoded by ICABPSII.

The anti-sense constructs of the present invention are under the control of inducible promoters, such that chlorophyll accumulation is not inhibited during early germination or in aerial tissue, requiring full photosynthetic capability.

Thus, according to one embodiment of the present invention there is provided an anti-sense construct comprising an anti-sense RNA sequence for the ICABPSII gene and a tissue-specific promoter.

In a further embodiment of the present invention there is provided an anti-sense construct comprising an anti-sense RNA sequence for the ICABPSII gene and a seed specific promoter.

In yet a further embodiment of the present invention there is provided a transgenic plant comprising an anti-sense RNA sequence for the ICABPSII gene and a tissue-specific promoter.

BRIEF DESCRIPTION OF THE DRAWINGS

These and other features of the invention will become more apparent from the following description in which reference is made to the appended drawings wherein:

FIG. 1 is the DNA sequence of the coding strand, the sense strand of BN-NH2, which encodes a type I chlorophyll a/b binding protein of the light harvesting antenna of PSII which corresponds to SEQ ID NO: 1. The corresponding amino acid sequence (not shown in the figure) is depicted as SEQ ID NO: 2. The Figure also contains some linker DNA nucleotides, GAATTC at the 5' end and GAATTC at the 3' end, which are not included in SEQ ID NO: 1.

DESCRIPTION OF PREFERRED EMBODIMENT

CAB Protein Gene

Figure 2:
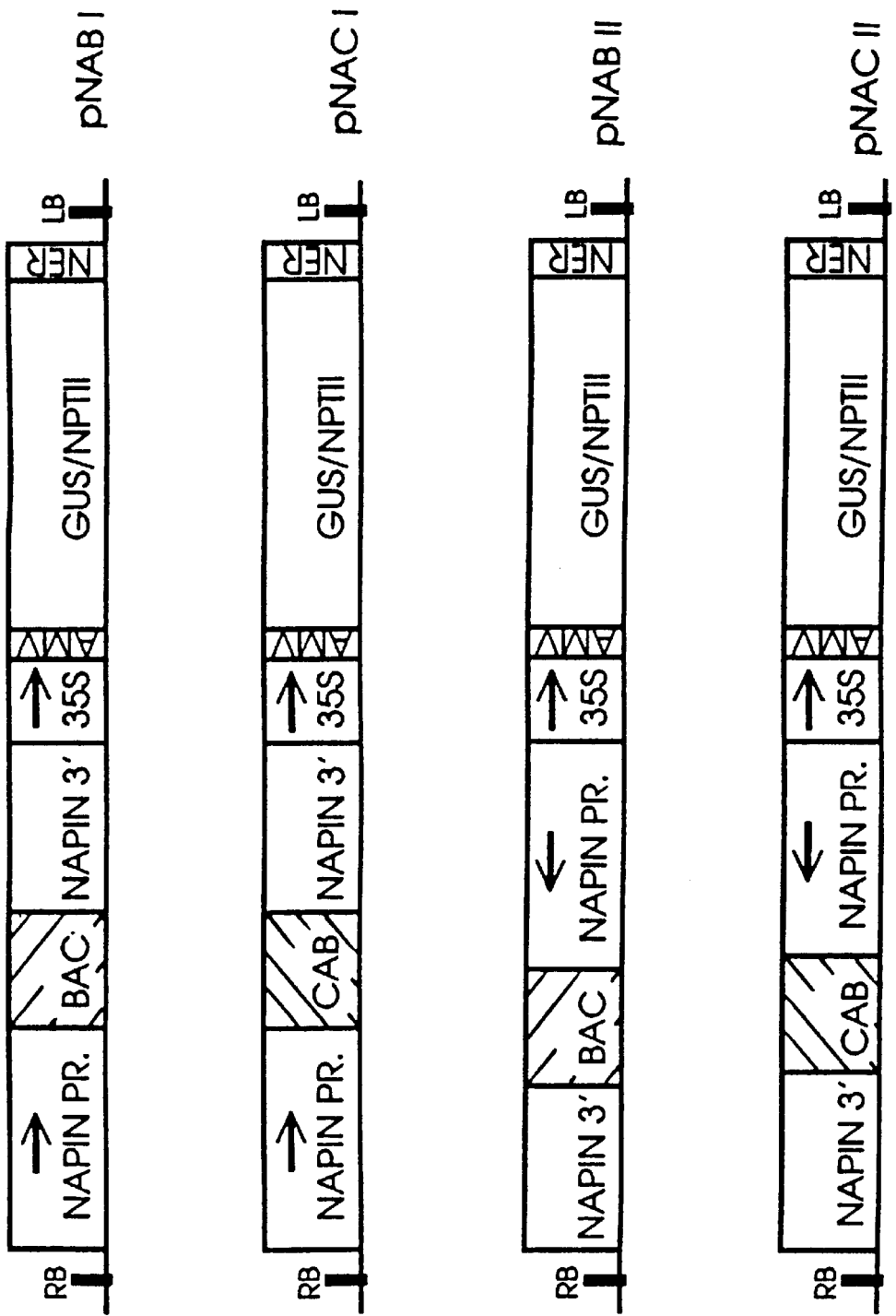
FIG. 2 is a map of the anti-sense (pNAB) and sense (pNAC) constructs of the present invention.

According to the present invention, any gene encoding chlorophyll a/b binding (CAB) proteins can be selected as a target to reduce the amount of chlorophyll a/b binding proteins, and thus reduce the chlorophyll content in the plants. The chlorophyll a/b binding proteins include LHCI of four different types, LHCII of types I to III, CP29, CP26, CP24 and early light-induced proteins (Green B. R., 1991, Trends Biochem. Sci., 16:181–186).

LHCII is the most abundant member of the family of chlorophyll a/b binding proteins, accounting for approximately 50% of total chlorophyll in the biosphere, and for the most chlorophyll b in green plants. Thus, a gene encoding LHCII could be a preferred gene for targeting to reduce the amount of chlorophyll a/b binding proteins, and thus the amount of chlorophyll content in the plants.

In all plant species examined to date, LHCII is encoded by a multi-gene family, consisting of at least five genes in

*Arabidopsis*, six genes in *Nicotiana tabacum*, eight genes in *N. plumbaginifolia*, and up to 15 genes in tomato (Jansson, S., et al., 1992, Plant Mol. Biol. Rep. 10:242–253). Thus, any of these genes could be a suitable target for controlling the amount of chlorophyll a/b protein, and thus the amount of chlorophyll in the plants.

The CAB protein of PSII encoded by ICABPSII is the major light harvesting antenna associated with PSII and contains 40 to 60% of the total chlorophyll in the mature chloroplast (Boardman et al., 1978, Current Topics in Bioenergetics, 8:35–109). Further, within PSII, there is a very high sequence homology between type I and type II CAB proteins (Pickersky et al., 1989, Plant Mol. Biol. 12:257). As such, targeting this gene could have a significant effect on altering the chlorophyll content.

In one embodiment of the present invention the cDNA corresponding to ICABPSII was isolated and sequenced from *B. napus*. This gene was used as a template for the production of an anti-sense RNA sequence. According to the present invention, other sources of the CAB protein gene can be used. The present invention is not restricted to the use of the CAB protein gene from *B. napus* or from other *Brassica sp*. Other sources of this gene include other Cruciferae, *Arabidopsis* and *Nicotiana* species.

In another example, a nuclear gene encoding a constituent polypeptide of the light-harvesting chlorophyll a/b protein complex has been isolated from pea (*Pisum sativum*) (Cashmore, A. R., Proc. Natl. Acad. Sci., 81:2960–2964) and an anti-sense construct of this gene could be used according to the present invention.

Anti-sense and Ribozyme Technology

The successful implementation of anti-sense RNA in developmental systems to inhibit the expression of unwanted genes has previously been demonstrated (Van der Krol et al., 1990 Plant Mol. Biol. 14:457; Visser et al., 1991, Mol. Gen. Genet. 225:289; Hamilton et al., 1990, Nature 346:284; Stockhaus et al., 1990, EMBO J. 9:3013; Hudson et al., 1992, Plant Physiol. 98:294). For example, polygalacturonase is responsible for fruit softening during the latter stages of ripening in tomato (Hiatt et al., 1989 in Genetic Engineering, Setlow, ed. p. 49; Sheehy et al., 1988, Proc. Natl. Acad. Sci. USA 85:8805; Smith et al., 1988, Nature 334:724). The integration of anti-sense constructs into the genome, under the control of the CaMV 35S promoter, has inhibited this softening, such that the product survives shipping and can be marketed at a higher price. Examination of the polygalacturonase mRNA levels showed a 90% suppression of gene expression, however the mechanism of suppression is not clear.

The anti-sense gene is a DNA sequence produced when a sense gene is inverted relative to its normal presentation for transcription. The "sense" gene refers to the gene which is being targeted for control using the anti-sense technology, in its normal orientation. An anti-sense gene may be constructed in a number of different ways provided that it is capable of interfering with the expression of a sense gene. Preferably, the anti-sense gene is constructed by inverting the coding region of the sense gene relative to its normal presentation for transcription to allow the transcription of its complement, hence the RNAs encoded by the anti-sense and sense gene are complementary. It is understood that a portion of the anti-sense gene incorporated into an anti-sense construct, of the present invention, may be sufficient to effectively interfere with the expression of a sense gene and thus the term "anti-sense gene" used herein encompasses any functional portion of the full length anti-sense gene. By the term "functional" it is meant to include a portion of the anti-sense gene which is effective in interfering with the expression of the sense gene.

It is further understood that the anti-sense constructs of the present invention include sequences that are "substantially homologous" to anti-sense sequence. Sequences are "substantially homologous" when at least about 80%, preferably at least about 90% and most preferably at least about 95% of the nucleotides match over a defined length of the molecule. Sequences that are "substantially homologous" include any substitution, deletion, or addition within the sequence. DNA sequences that are substantially homologous can be identified in Southern hybridization experiments, for example under stringent hybridization conditions (see Maniatis et al., in Molecular Cloning (A Laboratory Manual), Cold Spring Harbor Laboratory (1982) p 387 to 389). Thus the term "anti-sense gene" used herein encompasses said substantially homologous sequences of the native anti-sense gene.

The present invention is directed to a gene encoding a CAB binding protein, capable of binding chlorophyll, and methods directed to disrupting its expression. One embodiment of the present invention is directed to an anti-sense gene, which is prepared by inverting the coding region of the sense gene encoding the CAB protein of PSII (ICABPSII), and uses thereof.

Another method of interfering with CAB gene expression could involve the use of autocatalytic RNA molecules (ribozymes), which can also be used to target and repress the expression of specific plant genes (Gerlach et al., 1991, in Anti-sense nucleic acids and proteins 157). In fact, recent developments have greatly simplified the construction of catalytic anti-sense RNAs which combine the advantages of the anti-sense RNA and the ribozyme technologies in a single construct (Tabler and Tsagris, 1991, Gene 108:175). Smaller regions of homology are required for ribozyme catalysis, therefore this can promote the repression of different members of a large gene family if the cleavage sites are conserved. Together, these results point to the feasibility of utilizing anti-sense RNA and/or ribozymes as practical means of manipulating the composition of valuable crops. Thus, the term "anti-sense gene" is meant to include an anti-sense gene or portion thereof, in which a sequence encoding an autocatalytic RNA molecule (ribozyme) has been inserted within the anti-sense sequence.

Promoters

Most anti-sense constructs to date utilize constitutive high expression promoters. According to the present invention an inducible promoter is used, such that chlorophyll accumulation is not inhibited during early germination or in aerial tissue, requiring full photosynthetic capability.

An inducible promoter is a promoter that is capable of directly or indirectly activating transcription of one or more DNA sequences or genes in response to an inducer. In the absence of an inducer the DNA sequences or genes will not be transcribed. Typically the protein factor, that binds specifically to an inducible promoter to activate transcription, is present in an inactive form which is then directly or indirectly converted to the active form by the inducer. The inducer can be a chemical agent such as a protein, metabolite, a growth regulator, herbicide or a phenolic compound or a physiological stress imposed directly by heat, cold, salt, or toxic elements or indirectly through the action of a pathogen or disease agent such as a virus. A plant cell containing an inducible promoter may be exposed to an inducer by externally applying the inducer to the cell or plant such as by spraying, watering, heating or similar methods. If it is desirable to activate the expression of the anti-sense gene to a particular time during plant development, the inducer can be so applied at that time.

Examples of such inducible promoters include heat shock promoters, such as the inducible 70KD heat shock promoter of *Drosphilia melanogaster* (Freeling, M. et al., Ann. Rev. of Genetics, 19:297–323); a cold inducible promoter, such as the cold inducible promoter from *B. napus* (White, T. C. et al., 1994, Plant Physiol. 106); and the alcohol dehydrogenase promoter which is induced by ethanol (Nagao, R. T. et al., Miflin, B. J., Ed. Oxford Surveys of Plant Molecular and Cell Biology, Vol. 3, p 384–438, Oxford University Press, Oxford 1986).

Alternatively, if the sense gene is required for the normal development and function of the plant, a tissues specific promoter is preferable used to regulate the expression of the anti-sense gene. One such suitable promoter is the BCE.4 (*B. campestris* embryo) promoter which has been shown to direct high levels of expression in very early seed development (before the napin promoter). This is a period prior to storage product accumulation but of rapid pigment biosynthesis in the *Brassica* seed (derived from Johnson-Flanagan and Thiagarajah, 1989, J. Pl. Physiol. 136:180; Johnson-Flanagan et al., 1991, Physiol. Plant 81:301). Seed storage protein promoters have also been shown to direct a high level of expression in a seed-specific manner (Voelker et al., 1989, The Plant Cell 1:95; Altenbach et al., 1989, Plant Mol. Biol. 13:513; Lee et al., 1991, PNAS 99:6181). The napin promoter has been shown to direct oleosin gene expression in transgenic *Brassica*, such that oleosin accumulates to approximately 1% of the total seed protein (Lee et al., 1991, PNAS 99:6181). Further, expression was under temporal and tissue specific control similar to those for the napin gene. A seed coat specific promoter can also be useful to direct the transcription of the anti-sense gene of the present invention, for example the seed coat specific promoter from *N. tabacum* (Fobert, P. R. et al., 1994, The Plant Journal 6:567–577).

The specific promoter chosen will depend on the intended use of the anti-sense construct. For example if the anti-sense construct is to be used to reduce the green colour in seeds, for example in the seed of species from the Cruciferae family, any number of art recognized seed specific promoters would be suitable for said use. The anti-sense constructs of the present invention can also be used to reduce the chlorophyll content, and thus the green colour, of tissues other than seeds, such as in cauliflower heads and in certain fruits. Appropriate inducible and/or tissue specific promoters can be selected for such purpose.

In one embodiment of the present invention a napin promoter of the gNA class was used. gNA accumulation begins at 18 DPA (days postanthesis), reaches a peak at 27–33 days DPA and decreases steadily thereafter (Blundy et al., 1991, Plant Mol. Biol. 17:1099). Thus, transcription is directed before the period of maximum triacylglycerol biosynthesis and during pigment biosynthesis of the seed (Johnson-Flanagan and Thiagarajah, 1989, J. Pl. Physiol. 136:180; Johnson-Flanagan et al., 1991, Physiol. Plant 81:301). The accumulation of napin mRNA in developing seeds of *B. napus* c.v. Westar is demonstrated below in Table 1.

TABLE 1

| DPA | Moisture % | Pigment Seed ($\mu g/g$) | Napin mRNA |
|---|---|---|---|
| 7 | 80 | 1.5 | begin |
| 22 | 70 | 2.4 | (18d) |
| 28 | 60 | 2.48 | max |
| 37 | 50 | 1.58 | (33d) |
| 47 | 40 | ~0 | |

A further promoter which can be used according to the present invention directs oleosin biosynthesis. This is an oil body protein which accounts for up to 20% of the total protein in *Brassica* seed (Murphy et al., 1989, Bioch. J. 258:285). As oleosin gene expression is concurrent with triacylglycerol biosynthesis, the *Brassica* oleosin promoter would direct anti-sense CAB transcription at this developmental stage.

According to the present invention it may also be advisable to use a later seed specific promoter. An example of a later seed specific promoter is the cruciferin promoter. Cruciferin production peaks at approximately 40 DPA Finkelstein et al., 1985, Plant Physiol. 78:630). As such it would direct anti-sense CAB transcription during the later stages of triacylglycerol biosynthesis.

As has been discussed previously a sublethal frost during seed maturation results in a green seed problem in canola (*B. napus*). Thus a cold-inducible promoter would also be useful to induce anti-sense RNA production at a time which can be associated with renewed CAB protein and chlorophyll synthesis. An example of such a cold induced promoter from *B. napus* was discussed above (White, T. C. et al., 1994, Plant Physiol. 106).

The promoters of the present invention will be "operatively linked" to the anti-sense gene. The promoter sequence is operatively linked to the coding sequence in a cell when RNA polymerase will bind to the promoter and transcribe the coding sequence of the anti-sense gene into mRNA.

Anti-sense and Sense Constructs

The sense and anti-sense constructs (or vectors) of the present invention contain the nucleotide sequence coding for a chlorophyll a/b binding protein and the inverted sequence thereof, respectively. The constructs further contain an inducible promoter as defined above. Other DNA controlling sequences can also be included within the constructs of the present invention. These can include ribosome binding sites, polyadenylation signals, transcription termination sequences, upstream regulatory domains, enhancers and the like, all of which are well known and available in the art.

Other elements that can be included within the constructs of the present invention include a selectable marker gene which encodes a selection gene product which confers on cells or tissues a plant resistance to a chemical agent or physiological stress, such that the plant cells transformed with the constructs or plants containing such transformed plant cells may be used to select transformed plant cells. Many such selectable markers are known in the art, for example gentamycin, kanamycin, hygromycin, methotrexate, chlorsulfuron and bleomycin.

Anti-sense constructs utilizing different portions of the CAB coding region can also be used according to the present invention. As discussed above, the term "anti-sense gene" includes any functional portion of the full length anti-sense gene. The CAB gene contains two unique sites (BglII and AvrII) in a conserved region of the coding sequence which can be used to insert synthetic oligonucleotides coding for ribozyme cassettes (Tabler & Tsagris, 1991, Gene 109:175). These ribozyme cassettes can be incorporated in anti-sense CAB RNA constructs supplementing the effect of repression by irreversible cleavage of the target RNA. Various combinations of promoters, ribozymes and anti-sense RNA templates can be used according to the present invention for reducing chlorophyll content.

Transgenic Plants

Plant transformation can be according to Moloney et al. (1989, Plant Cell Rep. 8:238). *B. napus* L. cv. Westar can be germinated on MS plates under axenic conditions for 5 days, then the cotyledons can be cut and co-cultivated with *Agrobacterium tumefaciens* strain EHA101 for 3 days. Thereafter, the cotyledons can be moved onto kanamycin selection for 2 to 3 weeks. Putative transformants can be transferred to MS rooting medium, then to Redi-mix. At this time the plantlets will be grown in a misting chamber. Any other art known method for the production of transgenic plants can be used according to the present invention.

While this invention is described in detail with particular reference to preferred embodiments thereof, said embodiments are offered to illustrate but not limit the invention.

EXAMPLES

Example 1

Cloning of the Type I Chlorophyll a/b Binding Protein of the Light Harvesting Antenna of PSII from Spring *B. napus* L. cv. Jet neuf Plant Material and Growth Conditions Winter *B. napus* L. cv. Jet neuf was grown in controlled environment growth chambers at 20° C. under a 16 hour photoperiod with a light intensity of 250 $\mu$E m$^{-2}$s$^{-1}$ and 15° C. under 8 hours of darkness. For the cold treatment the plants were transferred to a growth chamber set at 2° C. (250 $\mu$E m$^{-2}$s$^{-1}$) and a 16 hour photoperiod) and left at this temperature for varying lengths of time.

Isolation of Total and messenger RNA:

Total RNA was isolated from leaf tissue using a phenol/chloroform extraction procedure (Sambrook et al., 1989, Molecular Cloning: A Laboratory Manual, Second Edition, New York: Cold Spring Harbor Laboratory Press). Poly (A)$^+$ RNA was isolated from the samples of total RNA by binding to Hybond-mAP paper (Amersham) according to the manufacturer's instructions.

Construction and Screening of cDNA Library

A cDNA library was prepared in the vector $\lambda$gt10 with EcoRI adaptors (Gubler and Hoffman, 1983, Gene, 26:263–269) using 10 $\mu$g poly (A)$^+$ RNA isolated from leaves of 4-week old *B. napus* cv Jet neuf plants that had been exposed to 2° C. for 4 days. Differential screening was carried out by preparing duplicate plaque lifts of the library using Nytran filters (0.45 $\mu$m, Schleicher & Scheull) and crosslinking of the DNA with UV light following the manufacturer's recommendations. Filters were hybridized with [$\alpha$-$^{32}$P]dATP (New England Nuclear) labelled ss cDNA prepared from poly (A)$^+$ RNA isolated from non-acclimated winter *B. napus* cv Jet neuf (grown at 24° C.) and plants acclimated at 2° C. for 1 week. Two recombinant $\lambda$gt10 clones which hybridized specifically to the ss cDNA probes, generated from poly(A)$^+$ RNA from non-acclimated plants, were isolated and purified. A 0.9 kb insert, BN-NH2, was excised from the vector by EcoRI digestion and subcloned in both orientations into the plasmid pGEM4 (Promega) to generate the plasmids pGEM4/NH2–4 and pGEM4/NH2–6.

DNA Sequencing

Nested deletions were constructed in the plasmids pGEM4/NH2–4 and pGEM4/NH2–6 using the Erase-a-base kit (Promega) following the manufacturer's instructions. The complete nucleotide sequence of both strands was determined using [$\alpha$-$^{35}$S]dATP and the T7 DNA Polymerase sequencing kit (Pharmacia) and sequence data analyzed using PCGene software. The sequence is shown in FIG. 1. Identification of BN-NH2 as a gene which encodes a type I chlorophyll a/b binding protein of the light harvesting antenna of PSII was determined by searching the following database: PC/GENE 6.5, SWISS-PROT.17, EMBL 25 (CD-ROM Release 4.0-IntelliGenetics, Inc.)

Example 2

Anti-sense Constructs

The anti-sense or sense CAB sequence was removed from the clone pNH2. pNH2 was a cDNA clone isolated by differential screening of a cold-acclimated winter *Brassica napus* cv Jet neuf cDNA library as described in Weretilnyk et al., (Plant Physiology, 101:171–177, 1993). pNH2 was down regulated during cold acclimation and subsequent sequencing identified the cDNA as 88–95% similar to the coding sequences of type I CAB1, CAB2 and CAB3 of *Arabidopsis* PSII. The sequence was subsequently mobilised into the XhoI (blunt ended) site between the napin promoter and napin polyadenylation signal sequence of the plasmid pGCN3223 obtained from Calgene. (McBride and Summerfelt, Plant Mol. Biol., 14:269 1990). The napin:CAB/BAC:napin 3' sequence was then excised as a partial HindII and mobilized into the plasmid pBI-FV3. pBI-FV3 was obtained from PBI Saskatoon and is a modification (EcoRI replaced by BamHI) of the binary vector described by Dattla et al., Gene, 101(2):239–246, 1991). The sense and anti-sense constructs are shown in FIG. 2. The resulting constructs were used for pNAC 1 and pNAB 1 transformation of *B. napus* cv Westar as described by Moloney et al. (Plant Cell Rep, 8:238, 1989).

Example 3

Transgenic Plants

Plants were independently transformed with the pNAB 1 construct (FIG. 2). Plants (T1 generation) were grown under standard growth conditions and total seed chlorophyll content was determined as described by Johnson-Flanagen, et al. (1990, J. Plant Physiol 136:385–390). The results are shown below in Table 2. Plants 2 and 3 show a significant reduction of chlorophyll (CHL) when compared to control plants.

TABLE 2

|  | $\mu$g CHL/G Fresh Weight | % | CHL/Seed ($\mu$g/G) | % |
|---|---|---|---|---|
| Control | 260 | 100 | 2.2 | 100 |
| Plant 1 | 217 | 82 | 2.3 | >100 |
| Plant 2 | 196 | 75 | 1.6 | 73 |
| Plant 3 | 152 | 58 | 1.2 | 53 |

All scientific publications and patent documents are incorporated herein by reference.

The present invention has been described with regard to preferred embodiments. However, it will be obvious to persons skilled in the art that a number of variations and modifications can be made without departing from the scope of the invention as described in the following claims.

SEQUENCE LISTING ( 1 ) GENERAL INFORMATION:

( i i i ) NUMBER OF SEQUENCES: 2

( 2 ) INFORMATION FOR SEQ ID NO: 1:

( i ) SEQUENCE CHARACTERISTICS:
      ( A ) LENGTH: 847 base pairs
      ( B ) TYPE: nucleic acid
      ( C ) STRANDEDNESS: double
      ( D ) TOPOLOGY: linear ( i x ) FEATURE:
      ( A ) NAME/KEY: CDS
      ( B ) LOCATION:8..811

( x i ) SEQUENCE DESCRIPTION: SEQ ID NO: 1:

```
CACTTCA ATG GCC TCT TCA ACA ATG GCT CTC TCC TCC CCT GCC TTC GCT         49
        Met Ala Ser Ser Thr Met Ala Leu Ser Ser Pro Ala Phe Ala
         1               5                   10

GGA AAG GCC GTG AAG CTT TCT CCT GCA GCA TCA GAA GTC CTT GGA AGC         97
Gly Lys Ala Val Lys Leu Ser Pro Ala Ala Ser Glu Val Leu Gly Ser
 15              20                  25                      30

GGC CGT GTG ACA ATG AGG AAG ACC GTC GCC AAG CCA AAG GGA CAA TCA        145
Gly Arg Val Thr Met Arg Lys Thr Val Ala Lys Pro Lys Gly Gln Ser
                 35                  40                  45

GGC AGC CCA TGG TAC GGT TTC GAA AGA GTC AAG TAC TTG GGT CCA TTC        193
Gly Ser Pro Trp Tyr Gly Phe Glu Arg Val Lys Tyr Leu Gly Pro Phe
             50                  55                  60

TCT GGC GAG CCA CCG AGC TAC CTT ACC GGA GAG TTC CCA GGA GAC TAC        241
Ser Gly Glu Pro Pro Ser Tyr Leu Thr Gly Glu Phe Pro Gly Asp Tyr
         65                  70                  75

GGA TGG GAC ACC GCA GGC CTC TCA GCC GAT CCC GAG ACA TTC GCA AGG        289
Gly Trp Asp Thr Ala Gly Leu Ser Ala Asp Pro Glu Thr Phe Ala Arg
     80                  85                  90

AAC CGT GAG CTA GAA GTT ATC CAC TGC AGG TGG GCC ATG CTT GGA GCC        337
Asn Arg Glu Leu Glu Val Ile His Cys Arg Trp Ala Met Leu Gly Ala
 95                 100                 105                 110

CTA GGC TGT GTC TTC CCG GAG TTG TTG GCT AGG AAC GGA GTC AAG TTC        385
Leu Gly Cys Val Phe Pro Glu Leu Leu Ala Arg Asn Gly Val Lys Phe
                115                 120                 125

GGA GAG GCG GTT TGG TTC AAG GCC GGC TCA CAG ATC TTC AGC GAA GGA        433
Gly Glu Ala Val Trp Phe Lys Ala Gly Ser Gln Ile Phe Ser Glu Gly
            130                 135                 140

GGA CTT GAC TAC TTG GGC AAC CCG GGC TTA GTC CAC GCT CAG AGC ATC        481
Gly Leu Asp Tyr Leu Gly Asn Pro Gly Leu Val His Ala Gln Ser Ile
        145                 150                 155

TTA GCC ATT TGG GCC ACT CAG GTG ATC CTC ATG GGA GCT GTT GAG GGT        529
Leu Ala Ile Trp Ala Thr Gln Val Ile Leu Met Gly Ala Val Glu Gly
    160                 165                 170

TAC AGA GTC GCC GGA GAG GGA CCA TTG GGA GAA GCA GAG GAC TTG CTA        577
Tyr Arg Val Ala Gly Glu Gly Pro Leu Gly Glu Ala Glu Asp Leu Leu
175                 180                 185                 190

TAC CCA GGA GGC AGC TTC GAC CCA TTG GGC CTT GCT ACC GAC CCA GAG        625
Tyr Pro Gly Gly Ser Phe Asp Pro Leu Gly Leu Ala Thr Asp Pro Glu
                195                 200                 205

GCT TTC GCC GAG TTG AAG GTG AAG GAG ATC AAG AAC GGG AGA TTG GCT        673
```

| | | | | | | | | | | | | | | | | |
|---|---|---|---|---|---|---|---|---|---|---|---|---|---|---|---|---|
| Ala | Phe | Ala | Glu<br>210 | Leu | Lys | Val | Lys | Glu<br>215 | Ile | Lys | Asn | Gly | Arg<br>220 | Leu | Ala | |
| ATG<br>Met | TTC<br>Phe | TCT<br>Ser<br>225 | ATG<br>Met | TTT<br>Phe | GGA<br>Gly | TTC<br>Phe | TTT<br>Phe<br>230 | GTT<br>Val | CAA<br>Gln | GCC<br>Ala | ATT<br>Ile | GTC<br>Val<br>235 | ACT<br>Thr | GGT<br>Gly | AAG<br>Lys | 721 |
| GGA<br>Gly | CCG<br>Pro<br>240 | TTG<br>Leu | GAG<br>Glu | AAC<br>Asn | CTT<br>Leu | GCT<br>Ala<br>245 | GAC<br>Asp | CAT<br>His | TTG<br>Leu | GCT<br>Ala | GAT<br>Asp<br>250 | CCA<br>Pro | GTC<br>Val | AAC<br>Asn | AAC<br>Asn | 769 |
| AAC<br>Asn<br>255 | GCT<br>Ala | TGG<br>Trp | GCC<br>Ala | TTC<br>Phe | GCC<br>Ala<br>260 | ACC<br>Thr | AAC<br>Asn | TTC<br>Phe | GTT<br>Val | CCC<br>Pro<br>265 | GGA<br>Gly | AAG<br>Lys | TGA<br>* | | | 811 |
| GCGAAGTTTT | ATTTTGTAAT | TTGCTTCAGT | CTTTTT | | | | | | | | | | | | | 847 |

(2) INFORMATION FOR SEQ ID NO: 2:

(i) SEQUENCE CHARACTERISTICS:
        (A) LENGTH: 267 amino acids
        (B) TYPE: amino acid
        (D) TOPOLOGY: linear (ii) MOLECULE TYPE: protein (xi) SEQUENCE DESCRIPTION: SEQ ID NO: 2:

| | | | | | | | | | | | | | | |
|---|---|---|---|---|---|---|---|---|---|---|---|---|---|---|
| Met<br>1 | Ala | Ser | Ser | Thr<br>5 | Met | Ala | Leu | Ser | Ser<br>10 | Pro | Ala | Phe | Ala | Gly Lys<br>15 |
| Ala | Val | Lys | Leu<br>20 | Ser | Pro | Ala | Ala | Ser<br>25 | Glu | Val | Leu | Gly | Ser<br>30 | Gly Arg |
| Val | Thr | Met<br>35 | Arg | Lys | Thr | Val | Ala<br>40 | Lys | Pro | Lys | Gly | Gln<br>45 | Ser | Gly Ser |
| Pro | Trp<br>50 | Tyr | Gly | Phe | Glu | Arg<br>55 | Val | Lys | Tyr | Leu | Gly<br>60 | Pro | Phe | Ser Gly |
| Glu<br>65 | Pro | Pro | Ser | Tyr | Leu<br>70 | Thr | Gly | Glu | Phe | Pro<br>75 | Gly | Asp | Tyr | Gly Trp<br>80 |
| Asp | Thr | Ala | Gly | Leu<br>85 | Ser | Ala | Asp | Pro | Glu<br>90 | Thr | Phe | Ala | Arg | Asn Arg<br>95 |
| Glu | Leu | Glu | Val<br>100 | Ile | His | Cys | Arg | Trp<br>105 | Ala | Met | Leu | Gly | Ala<br>110 | Leu Gly |
| Cys | Val | Phe<br>115 | Pro | Glu | Leu | Leu | Ala<br>120 | Arg | Asn | Gly | Val | Lys<br>125 | Phe | Gly Glu |
| Ala | Val<br>130 | Trp | Phe | Lys | Ala | Gly<br>135 | Ser | Gln | Ile | Phe | Ser<br>140 | Glu | Gly | Gly Leu |
| Asp<br>145 | Tyr | Leu | Gly | Asn | Pro<br>150 | Gly | Leu | Val | His | Ala<br>155 | Gln | Ser | Ile | Leu Ala<br>160 |
| Ile | Trp | Ala | Thr | Gln<br>165 | Val | Ile | Leu | Met | Gly<br>170 | Ala | Val | Glu | Gly | Tyr Arg<br>175 |
| Val | Ala | Gly | Glu<br>180 | Gly | Pro | Leu | Gly | Glu<br>185 | Ala | Glu | Asp | Leu | Leu<br>190 | Tyr Pro |
| Gly | Gly | Ser<br>195 | Phe | Asp | Pro | Leu | Gly<br>200 | Leu | Ala | Thr | Asp | Pro<br>205 | Glu | Ala Phe |
| Ala | Glu<br>210 | Leu | Lys | Val | Lys | Glu<br>215 | Ile | Lys | Asn | Gly | Arg<br>220 | Leu | Ala | Met Phe |
| Ser<br>225 | Met | Phe | Gly | Phe | Phe<br>230 | Val | Gln | Ala | Ile | Val<br>235 | Thr | Gly | Lys | Gly Pro<br>240 |
| Leu | Glu | Asn | Leu | Ala<br>245 | Asp | His | Leu | Ala | Asp<br>250 | Pro | Val | Asn | Asn | Asn Ala<br>255 |
| Trp | Ala | Phe | Ala<br>260 | Thr | Asn | Phe | Val | Pro<br>265 | Gly | Lys | | | | |

The embodiments of the invention in which an exclusive property or privilege is claimed are defined as follows:

1. A nucleic acid construct comprising:
   (a) an anti-sense gene of a sense gene encoding a chlorophyll a/b binding protein, or a portion of said anti-sense gene, wherein said sense gene is at least 90% similar to the nucleic acid sequence of SEQ ID NO: 1, and wherein said portion of said anti-sense gene is of a size capable of disrupting transcription of said chlorophyll a/b binding protein;
   (b) a seed specific promoter and a polyadenylation signal sequence both operatively linked to said anti-sense gene or portion thereof;
   wherein said construct is useful for reducing the level of chlorophyll a/b binding protein in seed tissue.

2. The construct according to claim 1, wherein the seed specific promoter is an inducible promoter.

3. The construct according to claim 2, wherein the inducible promoter is an ABA or Jasmonic acid-inducible promoter.

4. A transgenic plant containing a nucleic acid construct as defined in claim 1.

5. A method for reducing chlorophyll content in a seed by reducing an amount of chlorophyll a/b binding protein in said seed, comprising the steps of:
   (a) preparing the nucleic acid construct of claim 1 capable of disrupting expression of a chlorophyll a/b binding protein, and comprising a seed specific promoter; and
   (b) transforming a plant with said construct.

6. The construct according to claim 1, wherein the seed specific promoter is a BCE.4 promoter.

7. The construct according to claim 1, wherein the seed specific promoter is a napin promoter.

8. The construct according to claim 1, wherein the seed specific promoter is a tobacco seed-coat specific promoter.

9. A transgenic plant containing a nucleic acid construct as defined in claim 6.

10. A transgenic plant containing a nucleic acid construct as defined in claim 7.

11. A transgenic plant containing a nucleic acid construct as defined in claim 8.

12. A transgenic plant containing the nucleic acid construct of claim 2.

13. A transgenic plant containing the nucleic acid construct of claim 3.

14. The nucleic acid construct according to claim 1, wherein said sense gene is at least 91% similar to the nucleic acid sequence of SEQ ID NO: 1.

15. The nucleic acid construct according to claim 1, wherein said sense gene is at least 95% similar to the nucleic acid sequence of SEQ ID NO: 1.

* * * * *